United States Patent
Chen et al.

(10) Patent No.: US 9,169,172 B2
(45) Date of Patent: Oct. 27, 2015

(54) HYDROGENATION PROCESS

(71) Applicant: ExxonMobil Chemical Patents Inc., Baytown, TX (US)

(72) Inventors: Tan-Jen Chen, Kingwood, TX (US); Travis A. Reine, Slidell, LA (US); Keith H. Kuechler, Friendswood, TX (US); Terry E. Helton, Bethlehem, PA (US); Jihad M. Dakka, Whitehouse Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/394,524

(22) PCT Filed: Apr. 10, 2013

(86) PCT No.: PCT/US2013/035920
§ 371 (c)(1),
(2) Date: Oct. 15, 2014

(87) PCT Pub. No.: WO2013/165662
PCT Pub. Date: Nov. 7, 2013

(65) Prior Publication Data
US 2015/0065754 A1 Mar. 5, 2015

Related U.S. Application Data

(60) Provisional application No. 61/642,081, filed on May 3, 2012.

(30) Foreign Application Priority Data

Jun. 14, 2012  (EP) .................................... 12172044

(51) Int. Cl.
| | | |
|---|---|---|
| *C07C 45/53* | (2006.01) | |
| *C07C 37/08* | (2006.01) | |
| *C07C 2/66* | (2006.01) | |
| *C07C 5/05* | (2006.01) | |
| *C07C 2/74* | (2006.01) | |
| *C07C 5/03* | (2006.01) | |
| *C07C 407/00* | (2006.01) | |
| *C07C 7/163* | (2006.01) | |
| *B01J 23/44* | (2006.01) | |
| *B01J 23/46* | (2006.01) | |
| *B01J 23/75* | (2006.01) | |
| *B01J 23/755* | (2006.01) | |
| *B01J 35/00* | (2006.01) | |
| *B01J 35/08* | (2006.01) | |
| *B01J 37/00* | (2006.01) | |
| *C07C 409/14* | (2006.01) | |
| *B01J 21/04* | (2006.01) | |

(52) U.S. Cl.
CPC . *C07C 5/05* (2013.01); *B01J 23/44* (2013.01); *B01J 23/462* (2013.01); *B01J 23/75* (2013.01); *B01J 23/755* (2013.01); *B01J 35/008* (2013.01); *B01J 35/08* (2013.01); *B01J 37/0009* (2013.01); *C07C 2/74* (2013.01); *C07C 5/03* (2013.01); *C07C 7/163* (2013.01); *C07C 37/08* (2013.01); *C07C 45/53* (2013.01); *C07C 407/00* (2013.01); *C07C 409/14* (2013.01); *B01J 21/04* (2013.01); *C07C 2101/14* (2013.01); *C07C 2521/04* (2013.01); *C07C 2523/44* (2013.01)

(58) Field of Classification Search
CPC ............ C07C 45/53; C07C 37/08; C07C 2/66
USPC .......................... 568/376, 798, 799; 585/467
See application file for complete search history.

(56) References Cited

U.S. PATENT DOCUMENTS

| | | |
|---|---|---|
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,049,018 A | 4/2000 | Calabro et al. |
| 6,077,498 A | 6/2000 | Diaz Cabanas et al. |
| 6,720,462 B2 | 4/2004 | Kuhnle et al. |
| 6,756,030 B1 | 6/2004 | Rohde et al. |
| 2010/0249448 A1 | 9/2010 | Suzuki et al. |

FOREIGN PATENT DOCUMENTS

| | | |
|---|---|---|
| EP | 0 293 032 | 11/1988 |
| EP | 2 210 664 | 7/2010 |
| WO | WO 97/17290 | 5/1997 |
| WO | WO 2009/025939 | 2/2009 |
| WO | WO 2011/100013 | 8/2011 |

*Primary Examiner* — Sikarl Witherspoon
(74) *Attorney, Agent, or Firm* — Siwen Chen; Stephen A. Baehl

(57) ABSTRACT

The present invention relates to hydrogenation processes including: contacting a first composition with hydrogen under hydrogenation conditions, in the presence of an eggshell hydrogenation catalyst, wherein the first composition has: (i) greater than about 50 wt % of cyclohexylbenzene, the wt % based upon the total weight of the first composition; and (ii) greater than about 0.3 wt % of cyclohexenylbenzene, the wt % based upon the total weight of the first composition; and thereby obtaining a second composition having less cyclohexenylbenzene than the first composition. Other hydrogenation processes are also described.

23 Claims, No Drawings

HYDROGENATION PROCESS

PRIORITY CLAIM TO RELATED APPLICATIONS

This application is a National Stage Application of International Application No. PCT/US2013/035920 filed Apr. 10, 2013, which claims priority to and the benefit of U.S. Provisional Application Ser. No. 61/642,081 filed May 3, 2012 and European Application No. 12172044.5 filed Jun. 14, 2012, the disclosures of which are fully incorporated herein by their reference.

FIELD

The present invention relates to a hydrogenation process. In particular, the present invention relates to a hydrogenation process for converting cyclohexenylbenzene into cyclohexylbenzene. The present invention is useful, e.g., in producing phenol from benzene hydroalkylation.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene as feed and co-produces higher ketones, rather than acetone, may be an attractive alternative route to the production of phenols.

One such process proceeds via cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Although various methods are available for the production of cyclohexylbenzene, a preferred route is disclosed in U.S. Pat. No. 6,037,513, in which the cyclohexylbenzene is produced by hydroalkylating benzene with hydrogen in the presence of a bifunctional catalyst comprising a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product.

However, one or more steps of the process described above can produce substances that are detrimental to process efficiency. In particular, one of the problems associated with this process is that some amount of cyclohexenylbenzene (phenylcyclohexene) is inevitably formed during the oxidation/cleavage step. WO 2011/100013 discloses that cyclohexenylbenzene may be contacted with hydrogen in the presence of a hydrogenation catalyst under hydrogenation conditions to form cyclohexylbenzene (or phenylcyclohexane), which can then be recycled to produce phenol using processes described above. However, the hydrogenation of cyclohexenylbenzene back to cyclohexylbenzene often produces bicyclohexane (BCH) as an undesirable byproduct. BCH is particularly undesirable because BCH has a boiling point very close to that of cyclohexylbenzene, making them difficult to separate by conventional techniques, such as distillation. It is therefore highly desirable to minimize the formation of bicyclohexane (BCH) while hydrogenating cyclohexenylbenzene to cyclohexylbenzene.

Accordingly, there exists a need for highly active, highly selective processes of hydrogenating cyclohexenylbenzene to cyclohexylbenzene, thereby minimizing the production of unwanted byproducts, for example, BCH.

SUMMARY OF THE INVENTION

A first aspect of the present disclosure relates to hydrogenation processes comprising: contacting a first composition with hydrogen in the presence of an eggshell hydrogenation catalyst, wherein the first composition comprises:
   (i) greater than about 25 wt % of cyclohexylbenzene, the wt % based upon the total weight of the first composition; and
   (ii) greater than about 0.05 wt % in total of at least one olefin, the wt % based upon the total weight of the first composition; and
thereby obtaining a second composition having a lower concentration of the at least one olefin in total than the first composition.

A second aspect of the present disclosure relates to a process for producing phenol, the process comprising:
   (A) contacting a first feed comprising benzene with hydrogen in the presence of a hydroalkylation catalyst to produce a first effluent stream comprising cylcohexylbenzene and cyclohexenyl benzene;
   (B) oxidizing a second feed comprising at least a portion of the cylcohexylbenzene present in the first effluent stream to produce a second effluent stream comprising cyclohexylbenzene hydroperoxide;
   (C) cleaving a third feed comprising at least a portion of the cyclohexylbenzene hydroperoxide in the second effluent stream to produce a third effluent stream comprising phenol, cyclohexanone, and cyclohexenylbenzene; and
   (D) contacting a fourth feed comprising at least a portion of the cyclohexenylbenzene in the first effluent stream and/or the third effluent stream with hydrogen in the presence of an eggshell hydrogenation catalyst to produce a fourth effluent stream comprising cyclohexylbenzene.

A third aspect of the present disclosure relates to a process for producing phenol, the process comprising:
   (a) reacting benzene with hydrogen in the presence of a hydroalkylation catalyst under conditions effective to produce a hydroalkylation reaction effluent comprising cyclohexylbenzene and olefinic byproducts, benzene, and hydrogen;
   (b) removing a purge stream from the hydroalkylation reaction effluent, said purge stream comprising hydrogen and benzene;
   (c) washing the purge stream with a further stream containing cyclohexylbenzene to produce a benzene-depleted purge gas stream containing hydrogen and a wash stream containing cyclohexylbenzene and benzene;
   (d) separating an impure product stream comprising cyclohexylbenzene and olefinic byproducts from the hydroalkylation reaction effluent in the reacting step (a);
   (e) contacting the impure product stream of the separating step (d) with the benzene-depleted purge gas stream in the presence of an eggshell hydrogenation catalyst under conditions such that hydrogen in the benzene-depleted purge gas stream reacts with the olefinic by-products to produce a hydrogenated product stream and a hydrogen-depleted purge gas stream;

(f) purging said hydrogen-depleted purge gas stream;

(g) oxidizing at least a portion of the cyclohexylbenzene in said hydrogenated product stream of the contacting step (e) to cyclohexylbenzene hydroperoxide; and (h) cleaving at least a portion of the cyclohexylbenzene hydroperoxide produced in (g) to produce a cleavage product stream comprising phenol and cyclohexanone.

A fourth aspect of the present disclosure relates to a process for producing phenol, the process comprising:

(a) reacting benzene with hydrogen in the presence of a hydroalkylation catalyst under conditions effective to produce a hydroalkylation reaction effluent comprising cyclohexylbenzene and olefinic byproducts;

(b) removing a purge stream from the hydroalkylation reaction effluent, said purge stream comprising hydrogen and benzene;

(c) washing the purge stream with a further stream containing cyclohexylbenzene to produce a benzene-depleted purge gas stream containing hydrogen and a wash stream containing cyclohexylbenzene and benzene;

(d) separating an impure product stream comprising cyclohexylbenzene and at least a portion of the olefinic byproducts from the hydroalkylation reaction effluent;

(e) contacting the impure product stream with the benzene-depleted purge gas stream in the presence of a hydrogenation catalyst under conditions such that hydrogen in the benzene-depleted purge gas stream reacts with the olefinic byproducts to produce a hydrogenated product stream and a hydrogen-depleted purge gas stream;

(f) purging said hydrogen-depleted purge gas stream;

(g) oxidizing at least a portion of the cyclohexylbenzene in the hydrogenated product stream to cyclohexylbenzene hydroperoxide;

(h) cleaving at least a portion of the cyclohexylbenzene hydroperoxide produced in (g) to produce a cleavage product stream comprising phenol, cyclohexenylbenzene, and cyclohexanone;

(i) separating out a product stream comprising phenol and cyclohexanone and a recycle stream comprising cyclohexenylbenzene and residual cyclohexylbenzene; and (j) contacting the recycle stream with a gas stream comprising hydrogen in the presence of an eggshell hydrogenation catalyst under conditions such that hydrogen in the gas stream reacts with cyclohexenylbenzene to produce a hydrogenated recycle stream comprising cyclohexylbenzene and a hydrogen-depleted gas stream.

DETAILED DESCRIPTION OF THE EMBODIMENTS

Various specific embodiments, versions and examples of the present disclosure will now be described, including preferred embodiments and definitions that are adopted herein for purposes of understanding the claimed invention. While the following detailed description gives specific preferred embodiments, those skilled in the art will appreciate that these embodiments are exemplary only, and that the present disclosure can be practiced in other ways. For purposes of determining infringement, the scope of the present disclosure will refer to any one or more of the appended claims, including their equivalents, and elements or limitations that are equivalent to those that are recited. Any reference to the "invention" may refer to one or more, but not necessarily all, of the embodiments, of the inventions defined by the claims.

As used herein, the term "deplete" means "reduce." Thus, "a hydrogen-depleted stream" means a stream with reduced amount of hydrogen compared to the feed stream used to produce the hydrogen-depleted stream.

As used herein, the term "olefin" means a hydrocarbon material having a carbon-to-carbon double bond that is not part of an aromatic structure. The carbon-to-carbon double bond can be present in a ring or in a linear carbon chain. Thus, non-limiting examples of an olefin in the present disclosure include cyclohexene, cyclohexenylbenze, cyclopentene, methylcyclopentene, cyclopetenylbenzene, ethylene, 1-butene, propylene, and the like.

In the process of the present disclosure, when a reaction involves hydrogen, a gas mixture containing hydrogen and inert gas such as $N_2$, pure $H_2$, or a hydrogen source may be used. For example, in the hydroalkylation step of the process, a hydrogen source containing methane may be advantageously used. As used herein, a hydrogen source can be a mixture comprising hydrogen gas, or a starting material that can generate hydrogen gas under the reaction conditions it is subjected to. For example, a mixture of $H_2$ and $N_2$ can be a hydrogen source in certain embodiments. In other embodiments, $CH_4$ can be used as a hydrogen source as long as $CH_4$ disintegrates to form $H_2$ under the reaction conditions.

As used herein, the selectivity of the conversion of cyclohexenylbenzene to cyclohexylbenzene (SC1) is calculated as follows:

$$SC1 = \frac{\text{increase of cyclohexylbenzene}}{\text{decrease of cyclohexenylbenzene}} \times 100\%.$$

As used herein, the selectivity of the conversion of cyclohexenylbenzene to bicyclohexane (SC2) is calculated as follows:

$$SC2 = \frac{\text{increase of bicyclohexane}}{\text{decrease of cyclohexenylbenzene}} \times 100\%.$$

The inventors have surprisingly discovered that cyclohexenylbenzene (also known as phenylcyclohexene) can be converted to cyclohexylbenzene (also known as phenylcyclohexane) with high activity and high selectivity when using an eggshell hydrogenation catalyst, as described herein. Advantageously, these processes make very little of the undesired bicyclohexane byproduct. Bicyclohexane has a boiling point very close to that of cyclohexylbenzene. Accordingly, in streams where bicyclohexane is present, the yield of pure cyclohexylbenzene may be undesirably reduced. The inventive processes therefore, by producing little or no bicyclohexane, advantageously improve the yield of cyclohexylbenzene, as compared to conventional processes.

Hydrogenation Catalysts

Hydrogenation catalysts used in the hydrogenation processes discussed below are advantageously eggshell hydrogenation catalyst. In particular embodiments, it is within the scope of the present disclosure to have a dual stage hydrogenation process, in which two different hydrogenation catalysts are used, as long as at least one hydrogenation catalyst is an eggshell hydrogenation catalyst, as described below.

The Eggshell Hydrogenation Catalyst

Eggshell hydrogenation catalysts (also referred to as "eggshell-type" hydrogenation catalysts, or a hydrogenation catalyst having an eggshell structure) may be described as supported catalysts where the active metal component or its precursor is provided primarily (e.g., at least 50 wt %) as an outer layer on the surface of the support, as opposed to being dispersed throughout within the support. Compared with catalysts that have the active metal dispersed throughout the support, eggshell catalysts have a short diffusion pathway and are low in diffusion limitations.

For eggshell hydrogenation catalysts useful herein, the method of loading the active metal component on the carrier is not particularly restricted so long as it results in an egg-shell type supported catalyst. Specifically, the active metal component may be directly and/or indirectly loaded onto the surface layer of the support, after dissolution in an appropriate solvent (such as water or acetone, an inorganic acid or organic acid such as hydrochloric acid, nitric acid or acetic acid, or a mixture of two or more thereof).

Direct loading methods include impregnation including incipient wetness impregnation and spraying. Indirect loading methods include a stepwise process comprising first impregnating a carrier uniformly with an aqueous solution of a metal compound; causing the metal compound in the interior to migrate to the surface by alkali treatment, followed by reduction to provide the eggshell hydrogenation catalyst.

It is also within the scope of this invention to have a multiple loading technique, wherein several loading methods are combined, for example, the deposition of metal(s) on the support may be achieved by a combination of incipient wetness impregnation and spray-coating impregnation in series. When a multiple loading technique is used, the product from a loading step is desirably either dried or calcined at a temperature in the range from 200° C. to 800° C., for example, from 250° C. to 500° C., prior to carrying out the next loading. Additionally, where two or more metals are deposited onto a support, the deposition may occur in a single step, or in multiple steps. For example, metals may be deposited by alternately spray coating a solution of each metal compound onto the support or a mixed solution of the metal compounds may be spray coated onto the support.

The eggshell hydrogenation catalysts comprise at least one metal component and at least one support. The term "metal component" is used herein to include pure metallic metals, and/or metal compounds that may not be purely the elemental metal, but could, for example, be at least partly in another form, such as an oxide, hydride, or sulfide form. The weight % (wt %) of the metal component is herein defined as being measured as the metal present in metallic state based on the total weight of the catalyst composition irrespective of the form in which the metal component is present.

The metal component is advantageously selected from Groups 6 to 10 of the Periodic Table of Elements. The new notation for the Periodic Table Groups is used herein as described in *Chemical and Engineering News*, 63(5), 27 (1985). In certain embodiments, the at least one metal component comprises platinum, palladium, cobalt, nickel, ruthenium, or a mixture of two or more thereof. More advantageously, the metal component comprises palladium.

In certain embodiments, the eggshell hydrogenation catalyst comprises from about 0.1 wt % to about 10 wt % of the metal component, expressed as the nominal weight percentage of the metal component, converted to metallic state if not all in metallic state, on the basis of the total weight of the eggshell hydrogenation catalyst. Advantageously, the eggshell hydrogenation catalyst comprises from about 0.2 wt % to about 5 wt % of the metal component. In particular embodiments, the eggshell hydrogenation catalyst comprises from about 0.2 wt % to about 0.5 wt %, e.g., about 0.3 wt %, of the metal component. Advantageously, more than 50 wt %, such as more than 60 wt %, of the metal component is deposited in the peripheral outer layer of the support. More advantageously, more than 80 wt % of the metal component is deposited in the peripheral outer layer of the support. Even more advantageously, more than 90 wt % of the metal component is deposited in the peripheral outer layer of the support.

The support may be any support known in the art that is useful herein. More specifically, the support comprises at least one of aluminum oxide, silica, silicate, aluminosilicate, carbon, carbon nanotubes, and a mixture of two or more thereof. Advantageously, the support comprises silica, aluminum oxide, or a mixture of two or more thereof. The support may be calcined prior to the loading of the metal component.

Eggshell hydrogenation catalysts useful for the present disclosure are available commercially from a number of catalyst suppliers. For example, Alfa Aesar, 26 Parkridge Rd, Ward Hill, Mass. 01835, U.S.A.; Axens, 650 College Road East, Suite 1200, Princeton, N.J. 08540, U.S.A.; Johnson Matthey Inc., 456 Devon Park Drive, Wayne, Pa., 19087 U.S.A.; and Sud Chemie, Süd-Chemie AG, Lenbachplatz 6, 80333 Munich, Germany, each supplies one or more eggshell catalyst comprising precious metal supported by an inorganic material for hydrogenation reactions.

Hydrogenation Processes

Disclosed herein are hydrogenation processes comprising: contacting a first composition with hydrogen under hydrogenation conditions, in the presence of an eggshell hydrogenation catalyst, wherein the first composition comprises: (i) greater than about 25 wt % of cyclohexylbenzene, the wt % based upon the total weight of the first composition; and (ii) greater than about 0.10 wt % of cyclohexenylbenzene, the wt % based upon the total weight of the first composition; and thereby obtaining a second composition comprising lower concentration of cyclohexenylbenzene than the first composition.

In such processes, advantageously the contacting converts at least a portion of the cyclohexenylbenzene to cyclohexylbenzene. The hydrogenation of cyclohexenylbenzene to cyclohexylbenzene is known to produce bicyclohexane as an undesirable byproduct. It is highly desirable to minimize the formation of bicyclohexane while hydrogenating cyclohexenylbenzene to cyclohexylbenzene. In embodiments herein, using an eggshell hydrogenation catalyst, the cyclohexenylbenzene is selectively converted to cyclohexylbenzene. In preferred embodiments, the cyclohexenylbenzene is at least 50% more selectively converted to cyclohexylbenzene than to bicyclohexane (advantageously at least 60% more, e.g., at least 75% more, at least 85% more, at least 95% more, and even 98% more and 99% more). As used herein, "at least x % more selectively" means $100\% * (SC1-SC2)/SC1 \geq x$ %. In certain desirable embodiments, the second composition has a bicyclohexane concentration of CON(BCH)(2), expressed in terms of weight percentage of bicyclohexane on the basis of the total weight of the second composition, the first composition has a bicyclohexane concentration of CON(BCH)(1), expressed in terms of weight percentage of bicyclohexane on the basis of the total weight of the first composition, and $CON(BCH)(2)-CON(BCH)(1) \leq 0.50\%$, in certain embodiments $CON(BCH)(2)-CON(BCH)(1) \leq 0.40\%$, in certain embodiments $CON(BCH)(2)-CON(BCH)(1) \leq 0.30\%$, in certain embodiments $CON(BCH)(2)-CON(BCH)(1) \leq 0.20\%$, in certain embodiments $CON(BCH)(2)-CON(BCH)(1) \leq 0.10\%$, and in certain embodiments $CON(BCH)(2)-CON(BCH)(1) \leq 0.05\%$.

The first composition comprises greater than about 25 wt % of cyclohexylbenzene (in certain embodiments greater than about 30 wt %, e.g., greater than about 40 wt %, greater than about 50 wt %, greater than about 60 wt %, even greater than about 70 wt %, of cyclohexylbenzene), based upon the total weight of the first composition. The first composition also comprises greater than about 0.10 wt % of cyclohexenylbenzene (e.g., greater than about 0.20 wt %, greater than about 0.30 wt %, greater than about 0.40 wt %, greater than about 0.50 wt %, greater than about 0.60 wt %, greater than about 0.70 wt %, greater than about 0.80 wt %, greater than about 0.90 wt %, and even greater than about 1.00 wt %), based upon the total weight of the first composition. The first composition may also comprise cumene, sec-butylbenzene (SBB), or methylcyclopentyl benzene. While in certain advantageous embodiments the first composition is essentially free of bicyclohexane, it is possible that in certain other embodiments, the first composition comprises a small amount of bicyclohexane at a concentration of CON(BCH) (1), as indicated supra.

The first composition may be supplied from any source. For example, it may be supplied from a fresh source, produced during alkylation or hydroalkylation, and/or recycled from a step in the phenol production process. In various embodiments, the cyclohexenylbenzene is made during one or more of alkylation/hydroalkylation, oxidation, and cleavage steps of the phenol production process, which is described below.

The hydrogenation processes described herein have conditions including a temperature in the range from about 10° C. to about 400° C. (in certain embodiments in the range from about 40° C. to about 300° C., or from about 40° C. to about 250° C., or from 40° C. to about 200° C., such as from about 50° C. to about 120° C.). Suitable hydrogenation pressures are from about 10 kPag to about 7,000 kPag (such as from about 50 kPag to about 6000 kPag, or from about 100 kPag to about 5500 kPag, or from about 200 kPag to about 5000 kpag, or from about 400 kPag to about 4000 kPag, or from about 500 kPag to about 5,000 kPag, or from about 750 kPag to about 1500 kPag).

The present disclosure also relates to processes for producing phenol, the process comprising: (a) reacting benzene with hydrogen in the presence of a hydroalkylation catalyst under conditions effective to produce a hydroalkylation reaction effluent comprising cyclohexylbenzene, olefinic byproducts, benzene, and hydrogen; (b) removing a purge stream from the hydroalkylation reaction effluent, said purge stream comprising hydrogen and benzene; (c) washing the purge stream with a further stream containing cyclohexylbenzene to produce a benzene-depleted purge gas stream containing hydrogen and methane and a wash stream containing cyclohexylbenzene and benzene; (d) separating an impure product stream comprising cyclohexylbenzene and olefinic byproducts from the hydroalkylation reaction effluent; (e) contacting the impure product stream with the benzene-depleted purge gas stream in the presence of an eggshell hydrogenation catalyst under conditions such that hydrogen in the benzene-depleted purge gas stream reacts with the olefinic byproducts to produce a hydrogenated product stream and a hydrogen-depleted purge gas stream; and (f) purging said hydrogen-depleted purge gas stream.

In such embodiments, the olefinic byproducts of the hydroalkylation process include cyclohexenylbenzene, methylcyclopentenylbenze, and the like. In certain embodiments, the main olefinic byproduct is cyclohexenylbenzene.

The process above may further comprise recycling the wash stream to (d). The above process may yet further comprise (g) oxidizing at least a portion of the cyclohexylbenzene in said hydrogenated product stream to cyclohexylbenzene hydroperoxide; and (h) cleaving at least a portion of the cyclohexylbenzene hydroperoxide produced in (g) to produce phenol and cyclohexanone. In embodiments herein, steps (g) and (h) produce a cleavage product stream comprising phenol, cyclohexenylbenzene, and cyclohexanone. The cleavage product stream may also comprise residual unreacted cyclohexylbenzene.

The process above may further comprise recycling part of the cleavage product stream to (e) as part of the impure product stream, whereby the cyclohexenylbenzene from the cleavage product stream reacts with hydrogen in the gas stream in the presence of the eggshell hydrogenation catalyst under conditions sufficient to produce a hydrogenated recycle stream comprising cyclohexylbenzene and a hydrogen-depleted gas stream.

Advantageously, the impure product stream contains greater than 0.3 wt % of the olefinic by-products from the hydroalkylation, oxidation, and/or cleavage reaction effluents.

It is further within the scope of this invention to have a process comprising two or more catalysts. Exemplary embodiments relate to processes for producing phenol, the process comprising: (a) reacting benzene with hydrogen in the presence of a hydroalkylation catalyst under conditions effective to produce a hydroalkylation reaction effluent comprising cyclohexylbenzene, olefinic byproducts, benzene, and hydrogen; (b) removing a purge stream from the hydroalkylation reaction effluent, said purge stream comprising hydrogen and benzene; (c) washing the purge stream with a further stream containing cyclohexylbenzene to produce a benzene-depleted purge gas stream containing hydrogen and a wash stream containing cyclohexylbenzene and benzene; (d) separating an impure product stream comprising cyclohexylbenzene and olefinic byproducts from the hydroalkylation reaction effluent; (e) contacting the impure product stream with the benzene-depleted purge gas stream in the presence of a hydrogenation catalyst under conditions such that hydrogen in the benzene-depleted purge gas stream reacts with the olefinic byproducts to produce a hydrogenated product stream and a hydrogen-depleted purge gas stream; (f) purging said hydrogen-depleted purge gas stream; (g) oxidizing at least a portion of the cyclohexylbenzene in the hydrogenated product stream to cyclohexylbenzene hydroperoxide; (h) cleaving at least a portion of the cyclohexylbenzene hydroperoxide produced in (g) to produce a cleavage product stream comprising phenol, cyclohexenylbenzene, and cyclohexanone; (i) separating out a product stream comprising phenol and cyclohexanone and a recycle stream comprising cyclohexenylbenzene and residual cyclohexylbenzene; (j) contacting the recycle stream with a gas stream comprising hydrogen in the presence of an eggshell hydrogenation catalyst under conditions such that hydrogen in the gas stream reacts with cyclohexenylbenzene to produce a hydrogenated recycle stream comprising cyclohexylbenzene and a hydrogen-depleted gas stream.

In some embodiments, the process further consists of recycling the wash stream to (d).

In certain embodiments of the process, the cyclohexenylbenzene is at least 50% more selectively converted to cyclohexylbenzene than to bicyclohexane (advantageously at least 60% more, at least 75% more, at least 85% more, or at least 95% more).

In certain embodiments, the hydrogenation catalyst in the contacting step (e) is a non-eggshell hydrogenation catalyst. In certain other embodiments, the hydrogenation catalyst in the contacting step (e) is an eggshell hydrogenation catalyst, the same or different from the eggshell catalyst used in step (j). In other embodiments, the recycle stream of (j) is recycled to (e) as an impure product stream.

Phenol Production Process

An integrated method for the production of phenol is described herein. This method comprises hydroalkylation, dehydrogenation, oxidation, and/or cleavage steps.

Production of the Cyclohexylbenzene

The initial step of the integrated process for producing phenol is the selective hydrogenation of benzene in the presence of a hydroalkylation catalyst. The hydroalkylation reaction produces cyclohexylbenzene (CHB) according to the following reaction:

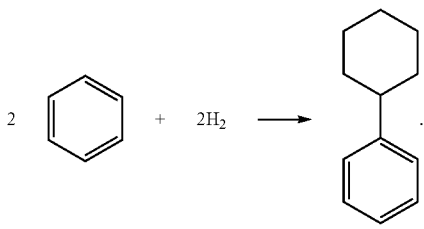 [SMILES: c1ccccc1 ; c1ccc(C2CCCCC2)cc1]

Any commercially available benzene feed can be used in the hydroalkylation reaction, but Advantageously the benzene has a purity level of at least 99 wt %. Similarly, although the hydrogen source is not critical, it is desirable that the hydrogen is at least 99 wt % pure.

Hydrogen can be supplied to the hydroalkylation step over a wide range of values. In certain embodiments, the molar ratio of hydrogen to benzene in the hydroalkylation feed is between about 0.15:1 and about 15:1, such as between about 0.4:1 and about 4:1, for example between about 0.4:1 and about 0.9:1.

In addition to the benzene and hydrogen, a diluent, which is substantially inert under hydroalkylation conditions, may be supplied to the hydroalkylation reaction in certain embodiments. In certain advantageous embodiments, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted byproduct of the hydroalkylation reaction.

Although the amount of diluent is not narrowly defined, in certain advantageous embodiments the diluent is added in an amount such that the weight ratio of the diluent to the aromatic compound is at least 1:100; for example at least 1:10, but no more than 10:1, advantageously no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated by reference in its entirety);

molecular sieves made from a common second degree building block, being a 2-dimensional tiling of such MWW framework topology unit cells, forming a monolayer of one unit cell thickness, advantageously one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Advantageously, the molecular sieve is selected from (a) MCM-49, (b) MCM-56, and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. In certain embodiments, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and in certain embodiments substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Desirably, the catalyst composite is produced by co-pelletization, in which a mixture of the molecular sieve and the metal-containing inorganic oxide are formed into pellets at high pressure (in certain embodiments, about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction is likely to contain some dicyclohexylbenzene byproduct. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also desirably effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as WO$_x$/ZrO$_2$, phosphoric acid, sulfated zirconia, and mixtures thereof. In certain embodiments, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, in certain embodiments, hydrogen is introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant byproduct of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst, in certain embodiments, comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and advantageously comprises silica. Suitable hydrogenation-dehydrogenation components (b) comprise at least one metal selected from Groups 6 to 10 of the Periodic Table of Elements, such as platinum, palladium and compounds and mixtures thereof. Desirably, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Desirably, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is, in certain embodiments, an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

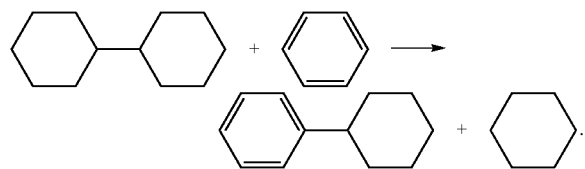

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to remove particulates, air that has been compressed and cooled to condense, and remove water or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxyl substituted cyclic imide or the N,N',N"-trihydroxyisocyanuric acid is employed in an amount between 0.0001 wt % to 15 wt %, such as between 0.001 wt % to 5 wt %, of the cyclohexylbenzene. The use of such oxidation catalysts in the manner disclosed herein conveniently facilitates a high selectivity to the desired cyclohexyl-1-phenyl-1-hydroperoxide, although other hydroperoxides may also be formed in varying quantities and be present in the oxidation effluent.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic byproducts that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation effluent. In certain embodiments, the oxidation effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation effluent. The oxidation effluent may further comprise imide catalyst and unreacted cyclohexylbenzene. For example, the oxidation effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation effluent.

At least a portion of the oxidation effluent may be subjected to a cleavage reaction, with or without undergoing any prior separation or treatment. For example, all or a fraction of the oxidation effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other absorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other absorbable components, and provide an oxidation composition reduced in oxidation catalyst or other absorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

In certain embodiments, the acid catalyst used in the cleavage reaction is at least partially soluble in the cleavage effluent, is stable at a temperature of at least 185° C. and has a lower volatility (higher normal boiling point) than cyclohexylbenzene. Desirably, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage effluent contains at least 50 parts-per-million-by-weight (wppm) and no greater than 5000 wppm of the acid catalyst, or at least 100 wppm to and no greater than 3000 wppm, or at least 150 wppm to and no greater than 2000 wppm of the acid catalyst, or at least 300 wppm and no greater than 1500 wppm of the acid catalyst, based upon total weight of the cleavage effluent.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12 and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage effluent may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. In certain embodiments, the polar solvent is added to the cleavage effluent such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage effluent includes cyclohexylbenzene in an amount of at least 50 wt %, or at least 60 wt %, or at least 65 wt %, or at least 70 wt %, or at least 80 wt %, or at least 90 wt %, based upon total weight of the cleavage effluent.

In certain embodiments, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage effluent is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Separation of Phenol from Cleavage Effluent

The major products of the cleavage reaction of cyclohexyl-1-phenyl-1-hydroperoxide are phenol and cyclohexanone which can be separated by using, e.g., an extractive distillation process.

EXAMPLES

Example 1

The Present Disclosure

A first eggshell catalyst containing 0.3 wt % Pd on an aluminum oxide support was used. The support had a spherical/spheroidal shape.

A downflow reactor was equipped with the first eggshell hydrogenation catalyst. The catalyst was tested at 5 hr$^{-1}$ WHSV, 50° C., and 165 psig. The feed consisted of 0.5 wt % 1-phenylcyclohexene in 99.5% phenylcyclohexane. The catalyst was allowed to perform for 6 days on stream. Conversion of phenylcyclohexene to phenylcyclohexane is reported in Table 1, below. The amount of bicyclohexane (BCH) made is also reported in Table 1.

Example 2

Comparative Example

A non-eggshell catalyst containing 0.5 wt % Pd on an aluminum oxide support was used.

A downflow reactor was equipped with the non-eggshell (conventional) catalyst. The catalyst was tested at 5 hr$^{-1}$ WHSV, 50° C., and 165 psig. The feed consisted of 0.5 wt % 1-phenylcyclohexene in 99.5% phenylcyclohexane. The catalyst was allowed to perform for 6 days on stream. Conversion of phenylcyclohexene to phenylcyclohexane is reported in Table 1, below. The amount of bicyclohexane (BCH) made is also reported in Table 1.

Example 3

The Present Disclosure

A second commercial eggshell catalyst containing 0.3 wt % Pd on alumina support was evaluated. The catalyst had a non-spherical shape of an extrudate, which was different from the first eggshell catalyst.

A downflow reactor was equipped with the second eggshell catalyst. The catalyst was tested at 4 hr$^{-1}$ WHSV, 65° C., and 150 psig. The feed consisted of 1.0 wt % 1-phenylcyclohexene in 99.0% phenylcyclohexane. The catalyst was allowed to perform for 6 days on stream. Conversion of phenylcyclohexene to phenylcyclohexane is reported in Table 1, below.

TABLE 1

| Performance of Catalyst | | | |
| --- | --- | --- | --- |
|  | Example 1 | Example 2 | Example 3 |
| Conversion (Wt %) | 99.1 | 77.9 | 100.0 |
| BCH (ppm) | 0.1 | 15 | 58.0 |

As can be seen from Table 1, both the first and second eggshell catalysts were very active, demonstrating 99.1 wt % and 100.0 wt % conversion, respectively. Both were superior to that of the conventional Pd/Al$_2$O$_3$ catalyst, which demonstrated 77.9 wt % conversion, even though the conventional non-eggshell catalyst contained a higher loading of Pd than the first eggshell catalyst (0.5 wt % vs. 0.3 wt %). The selectivity of the eggshell catalyst is also excellent; particularly with regard to the first eggshell catalyst, with BCH produced being 0.1 wppm. This is in marked contrast to the conventional Pd catalyst, which produced 15 ppm BCH.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the present disclosure have been illustrated and described, various modifications can be made without departing from the spirit and scope of the present disclosure. Accordingly, it is not intended that the invention be limited thereby. Likewise, the term "comprising" is considered synonymous with the term "including" for purposes of Australian law. Likewise, "comprising" encompasses the terms "consisting essentially of," "is," and "consisting of" and anyplace "comprising" is used "consisting essentially of," "is," or "consisting of" may be substituted therefor.

We claim:

1. A hydrogenation process comprising:
(I) contacting a first composition with hydrogen in the presence of an eggshell hydrogenation catalyst, thereby obtaining a second composition having a lower concentration of the at least one olefin in total than the first composition;
wherein the first composition comprises:
(i) greater than about 25 wt % of cyclohexylbenzene, the wt % based upon the total weight of the first composition; and
(ii) greater than about 0.05 wt % in total of at least one olefin, the wt % based upon the total weight of the first composition, and
further wherein the eggshell hydrogenation catalyst comprises at least one metal component selected from Groups 6 to 10 of the Periodic Table of Elements and at least one support, such that more than 50 wt % of the at least one metal component present in the hydrogenation catalyst is deposited in a peripheral outer layer of the support.

2. The process of claim 1, wherein the at least one olefin comprises cyclohexenylbenzene, the cyclohexenylbenzene has a concentration greater than about 0.05 wt % based on the total weight of the first composition.

3. The process of claim 2, wherein in the contacting step (I), at least a portion of the cyclohexenylbenzene is converted into cyclohexylbenzene.

4. The process of claim 1, wherein in the contacting step (I), the selectivity of the conversion of cyclohexenylbenzene to cyclohexylbenzene is SC1, the selectivity of the conversion of cyclohexenylbenzene to bicyclohexane is SC2, and (SC1-SC2)/SC1≥0.50.

5. The process of claim 1, wherein the concentration of bicyclohexane in the second composition, expressed in terms of weight percentage of the total weight of the second composition, is CON(BCH)(2), the concentration of bicyclohexane in the first composition, expressed in terms of weight percentage of the total weight of the first composition, is CON(BCH)(1), and CON(BCH)(2)−CON(BCH)(1)≤0.50%.

6. The process of claim 1, wherein the contacting step (I) is conducted at a temperature in a range from about 40° C. to about 200° C. and a pressure in the range from 700 kPa to 1000 kPa.

7. The process of claim 1, wherein the at least one metal component comprises palladium, cobalt, nickel, ruthenium, or a mixture of two or more thereof.

8. The process of claim 1, wherein the support comprises at least one of aluminum oxide, silica, silicate, aluminosilicate, carbon, carbon nanotubes, and a mixture of two or more thereof.

9. The process of claim 1, wherein the eggshell hydrogenation catalyst comprises about 0.1 wt % to about 10 wt % of the metal component, the wt % based upon the total weight of the eggshell hydrogenation catalyst including the metal and the support.

10. A process for producing phenol and/or cyclohexanone, the process comprising:
(A) contacting a first feed comprising benzene with hydrogen in the presence of a hydroalkylation catalyst to produce a first effluent stream comprising cylcohexylbenzene and cyclohexenyl benzene;
(B) oxidizing a second feed comprising at least a portion of the cylcohexylbenzene present in the first effluent stream to produce a second effluent stream comprising cyclohexylbenzene hydroperoxide;
(C) cleaving a third feed comprising at least a portion of the cyclohexylbenzene hydroperoxide in the second effluent stream to produce a third effluent stream comprising phenol, cyclohexanone and cyclohexenylbenzene; and
(D) contacting a fourth feed comprising at least a portion of the cyclohexenylbenzene in the first effluent stream and/or the third effluent stream with hydrogen in the presence of an eggshell hydrogenation catalyst to produce a fourth effluent stream comprising cyclohexylbenzene;
wherein the eggshell hydrogenation catalyst comprises at least one metal component selected from Groups 6 to 10 of the Periodic Table of Elements and at least one support, such that more than 50 wt % of the at least one metal component present in the hydrogenation catalyst is deposited in a peripheral outer layer of the support.

11. The process of claim 10, wherein at least a portion of the cyclohexylbenzene in the fourth effluent stream is provided into the second feed of the oxidizing step (B).

12. The process of claim 10, wherein in the contacting step (D), the fourth feed comprises at least a portion of the cyclohexenylbenzene in both of the first effluent stream and the third effluent stream.

13. The process of claim 10, wherein in the oxidizing step (B), the second feed has a concentration of cyclohexenylbenzene of at most 0.05 wt % of the total weight of the second feed.

14. A process for producing phenol and/or cyclohexanone, the process comprising:
(a) reacting benzene with hydrogen in the presence of a hydroalkylation catalyst under conditions effective to produce a hydroalkylation reaction effluent comprising cyclohexylbenzene and olefinic byproducts, benzene, and hydrogen;
(b) removing a purge stream from the hydroalkylation reaction effluent, said purge stream comprising hydrogen and benzene;
(c) washing the purge stream with a further stream containing cyclohexylbenzene to produce a benzene-depleted purge gas stream containing hydrogen and a wash stream containing cyclohexylbenzene and benzene;
(d) separating an impure product stream comprising cyclohexylbenzene and olefinic byproducts from the hydroalkylation reaction effluent in the reacting step (a);
(e) contacting the impure product stream of the separating step (d) with the benzene-depleted purge gas stream in the presence of an eggshell hydrogenation catalyst under conditions such that hydrogen in the benzene-depleted purge gas stream reacts with the olefinic by-products to produce a hydrogenated product stream and a hydrogen-depleted purge gas stream;
wherein the eggshell hydrogenation catalyst comprises at least one metal component selected from Groups 6 to 10 of the Periodic Table of Elements and at least one support, such that more than 50 wt % of the at least one metal component present in the hydrogenation catalyst is deposited in a peripheral outer layer of the support;
(f) purging said hydrogen-depleted purge gas stream;
(g) oxidizing at least a portion of the cyclohexylbenzene in said hydrogenated product stream of the contacting step (e) to cyclohexylbenzene hydroperoxide; and
(h) cleaving at least a portion of the cyclohexylbenzene hydroperoxide produced in (g) to produce a cleavage product stream comprising phenol and cyclohexanone.

15. The process of claim 14, wherein the wash stream in the washing step (c) is recycled to the separating step (d).

16. The process of claim 14, wherein the cleavage product stream in the cleaving step (h) comprises cyclohexenylbenzene.

17. The process of claim 14, wherein the cyclohexenylbenzene from the cleavage product stream in the cleaving step (h) is recycled to the contacting step (e) and into the impure product stream of the contacting step (e).

18. The process of claim 14, wherein the impure product stream in the contacting step (e) contains greater than 0.10 wt % of olefinic byproducts from the hydroalkylation, oxidation, and/or cleavage reaction effluents.

19. The process of claim 14, wherein the eggshell hydrogenation catalyst comprises about 0.10 wt % to about 10.0 wt % of the at least one metal component, the wt % based upon the total weight of the hydrogenation catalyst including the metal component and the support.

20. A process for producing phenol and/or cvclohexanone, the process comprising:
(a) reacting benzene with hydrogen in the presence of a hydroalkylation catalyst under conditions effective to produce a hydroalkylation reaction effluent comprising cyclohexylbenzene and olefinic byproducts;
(b) removing a purge stream from the hydroalkylation reaction effluent, said purge stream comprising hydrogen and benzene;
(c) washing the purge stream with a further stream containing cyclohexylbenzene to produce a benzene-depleted purge gas stream containing hydrogen and a wash stream containing cyclohexylbenzene and benzene;
(d) separating an impure product stream comprising cyclohexylbenzene and at least a portion of the olefinic byproducts from the hydroalkylation reaction effluent;
(e) contacting the impure product stream with the benzene-depleted purge gas stream in the presence of a hydrogenation catalyst under conditions such that hydrogen in the benzene-depleted purge gas stream reacts with the olefinic byproducts to produce a hydrogenated product stream and a hydrogen-depleted purge gas stream;
(f) purging said hydrogen-depleted purge gas stream;
(g) oxidizing at least a portion of the cyclohexylbenzene in the hydrogenated product stream to cyclohexylbenzene hydroperoxide;
(h) cleaving at least a portion of the cyclohexylbenzene hydroperoxide produced in (g) to produce a cleavage product stream comprising phenol, cyclohexenylbenzene, and cyclohexanone;
(i) separating out a product stream comprising phenol and cyclohexanone and a recycle stream comprising cyclohexenylbenzene and residual cyclohexylbenzene; and
(j) contacting the recycle stream with a gas stream comprising hydrogen in the presence of an eggshell hydrogenation catalyst under conditions such that hydrogen in the gas stream reacts with cyclohexenylbenzene to produce a hydrogenated recycle stream comprising cyclohexylbenzene and a hydrogen-depleted gas stream;

wherein the eggshell hydrogenation catalyst comprises at least one metal component selected from Groups 6 to 10 of the Periodic Table of Elements and at least one support, such that more than 50 wt % of the at least one metal component present in the hydrogenation catalyst is deposited in a peripheral outer layer of the support.

21. The process of claim 20, wherein the selectivity of the conversion of cyclohexenylbenzene to cyclohexylbenzene is SC1, the selectivity of the conversion of cyclohexenylbenzene to bicyclohexane is SC2, and (SC1-SC2)/SC1≥0.50.

22. The process of claim 20, wherein the impure product stream contains greater than 1.0 wt % of the olefinic byproducts from the hydroalkylation reaction effluent.

23. The process of claim 20, wherein the hydrogenation catalyst of the contacting step (e) and/or the eggshell hydrogenation catalyst of the contacting step (j) comprise from about 0.1 wt % to about 10 wt % of a metal component selected from palladium, cobalt, nickel, ruthenium, or a mixture of two or more thereof, the wt % based upon the total weight of the hydrogenation catalyst.

* * * * *